United States Patent
Minh et al.

(10) Patent No.: US 6,559,639 B2
(45) Date of Patent: *May 6, 2003

(54) ESTIMATING PERMEABILITY WITHOUT DETERMINATING A DISTRIBUTION OF RELAXATION TIMES

(75) Inventors: Chanh Cao Minh, Katy; Nicholas J. Heaton; Abdurrahman Sezginer, both of Houston, all of TX (US)

(73) Assignee: Schlumberger Technology Corporation, Sugar Land, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/397,581

(22) Filed: Sep. 16, 1999

(65) Prior Publication Data

US 2003/0011366 A1 Jan. 16, 2003

Related U.S. Application Data

(60) Provisional application No. 60/102,863, filed on Oct. 2, 1998, and provisional application No. 60/114,928, filed on Jan. 6, 1999.

(51) Int. Cl.[7] .................................................. G01V 3/00
(52) U.S. Cl. ...................................................... 324/303
(58) Field of Search ............................... 324/303, 300, 324/314, 309, 307, 313, 312

(56) References Cited

U.S. PATENT DOCUMENTS

| 4,412,179 A | 10/1983 | Brown |
| 4,728,892 A | 3/1988 | Vinegar et al. |
| 4,933,638 A | 6/1990 | Kenyon et al. |
| 5,023,551 A | 6/1991 | Kleinberg et al. |
| 5,289,124 A | 2/1994 | Jerosch-Herold et al. |
| 5,387,865 A | 2/1995 | Jerosch-Herold et al. |
| 5,570,019 A | 10/1996 | Moonen et al. |
| 5,596,274 A | 1/1997 | Sezginer |
| 6,008,645 A | 12/1999 | Bowers et al. |
| 6,147,489 A * | 11/2000 | Freedman et al. .......... 324/303 |

FOREIGN PATENT DOCUMENTS

| FR | 2729228 | 7/1996 |
| FR | 2 729 228 A1 | 7/1996 |
| WO | WO 92/21045 | 11/1992 |
| WO | WO 96/12976 | 5/1996 |

OTHER PUBLICATIONS

J. A. Brown, J. A. Jackson & A. R. Koelle, Western Gas Sands Project Los Alamos NMR Well Logging Tool Development, Los Alamos National Laboratory Final Report LA–10374–PR, Los Alamos, New Mexico (Mar. 1985).

* cited by examiner

Primary Examiner—Edward Lefkowitz
Assistant Examiner—Tiffany A. Fetzner
(74) Attorney, Agent, or Firm—Kevin P. McEnaney; Brigitte L. Jeffery; John J. Ryberg

(57) ABSTRACT

A permeability estimation technique for use with spin echo signals that are received from a sample includes summing indications of the amplitudes of the spin echo signals. The results of the summing are used to determine an indication of a permeability of the sample, without using a distribution of relaxation times in the determination. The products of indications of the amplitudes of the spin echo signals may be summed, and the results of the summing may be used to determine an indication of a permeability of the sample, without using a distribution of relaxation times in the determination.

15 Claims, 7 Drawing Sheets

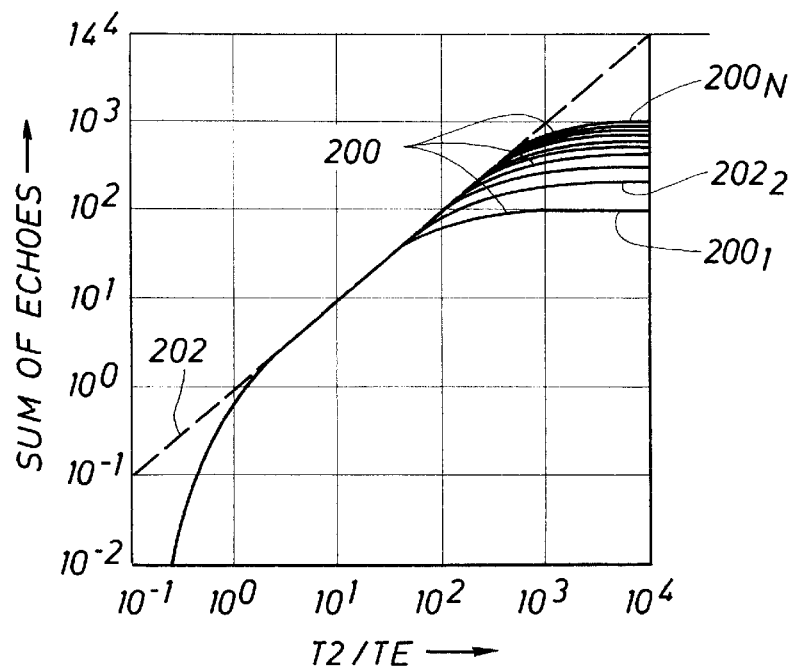
FIG. 7
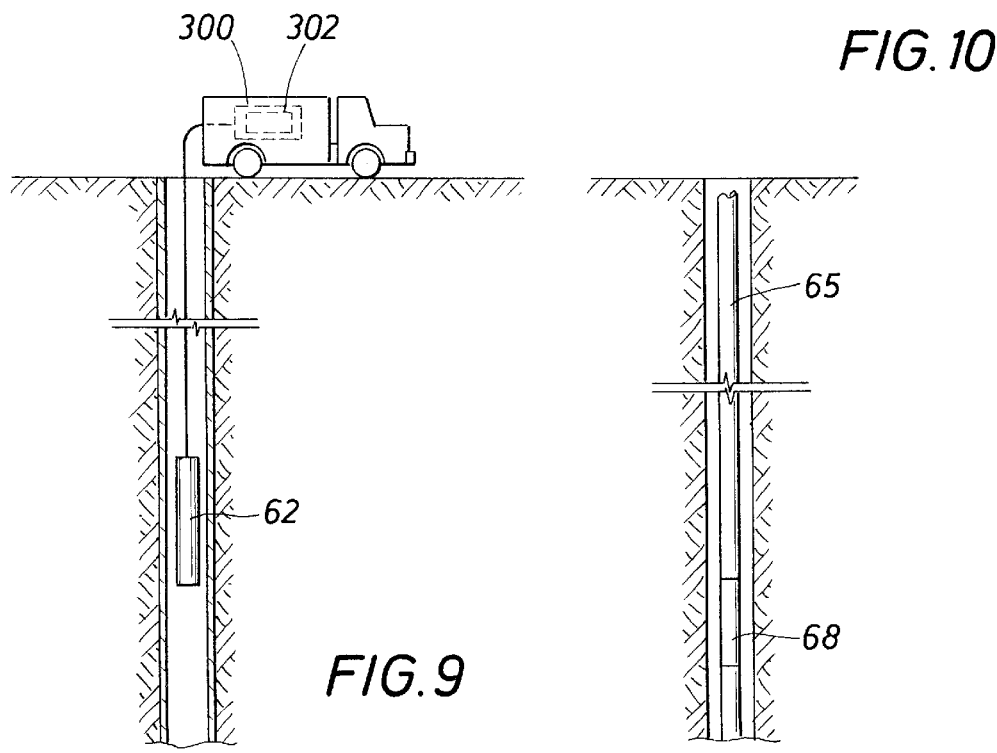
FIG. 10
FIG. 9

US 6,559,639 B2

ESTIMATING PERMEABILITY WITHOUT DETERMINATING A DISTRIBUTION OF RELAXATION TIMES

This application claims priority under 35 U.S.C. §119 to U.S. Provisional Patent Application Ser. No. 60/102,863, filed on Oct. 2, 1998, and U.S. Provisional Patent Application Ser. No. 60/114,928, filed on Jan. 6, 1999.

BACKGROUND

This invention relates to estimating permeability.

Nuclear magnetic resonance (NMR) measurements typically are performed to investigate properties of a sample. For example, an NMR wireline or logging while drilling (LWD) downhole tool may be used to measure properties of subterranean formations. In this manner, the typical downhole NMR tool may, for example, provide a lithology-independent measurement of the porosity of a particular formation by determining the total amount of hydrogen present in fluids of the formation. Equally important, the NMR tool may also provide measurements that indicate the dynamic properties and environment of the fluids, as these factors may be related to petrophysically important parameters. For example, the NMR measurements may provide information that may be used to derive the permeability of the formation and viscosity of fluids contained within the pore space of the formation. It may be difficult or impossible to derive this information from other conventional logging arrangements. Thus, it is the capacity of the NMR tool to perform these measurements that makes it particularly attractive versus other types of downhole tools.

Typical NMR logging tools include a magnet that is used to polarize hydrogen nuclei (protons) in the formation and a transmitter coil, or antenna, that emits radio frequency (RF) pulses. A receiver antenna may measure the response (indicated by a received RF signal) of the polarized hydrogen to the transmitted pulses. Quite often, the transmitter and receiver antennae are combined into a single transmitter/receiver antenna.

The NMR techniques employed in current NMR tools typically involve some variant of a basic two step sequence that includes a polarization time and thereafter using an acquisition sequence. During the polarization time (often referred to as a "wait time"), the protons in the formation polarize in the direction of a static magnetic field (called $B_0$) that is established by a permanent magnet (of the NMR tool). The growth of nuclear magnetization M(t) (i.e., the growth of the polarization) is characterized by the "longitudinal relaxation time" (called T1) of the fluid and its equilibrium value (called $M_0$). When the specimen is subject to a constant field for a duration $t_p$, the longitudinal magnetization is described by the following equation:

$$M(t_p) = M_0 \left(1 - e^{\frac{-t_p}{T1}}\right) \quad \text{(Eq. 1)}$$

The duration of the polarization time may be specified by the operator (conducting the measurement) and includes the time between the end of one acquisition sequence and the beginning of the next. For a moving tool, the effective polarization time also depends on tool dimensions and logging speed.

Referring to FIG. 1, as an example, a sample (in the formation under investigation) may initially have a longitudinal magnetization 10 (called $M_Z$) of approximately zero. The zero magnetization may be attributable to a preceding acquisition sequence, for example. However, in accordance with Equation (Eq.) 1, the $M_Z$ magnetization 10 (under the influence of the $B_0$ field) increases to a magnetization level (called M(tp(1))) after a polarization time tp(1) after zero magnetization. As shown, after a longer polarization time tp(2) from zero magnetization, the $M_Z$ magnetization 10 increases to a higher M(tp(2)) magnetization level.

An acquisition sequence (the next step in the NMR measurement) typically begins after the polarization time. For example, an acquisition sequence may begin at time tp(1), a time at which the $M_Z$ magnetization 10 is at the M(tp(1)) level. At this time, RF pulses are transmitted from a transmitter antenna of the NMR tool. The pulses, in turn, produce spin echo signals 16 that appear as a RF signal to the NMR tool. A receiver antenna (that may be formed from the same coil as the transmitter antenna) receives the spin echo signals 16 and stores digital signals that indicate the spin echo signals 16. The initial amplitudes of the spin echo signals 16 indicate a point on the $M_Z$ magnetization 10 curve, such as the M(tp(1)) level, for example. Therefore, by conducting several measurements that have different polarization times, points on the $M_Z$ magnetization 10 curve may be derived, and thus, the T1 time for the particular formation may be determined.

As a more specific example, for the acquisition sequence, a typical logging tool may emit a pulse sequence based on the CPMG (Carr-Purcell-Meiboom-Gill) pulse train. The application of the CPMG pulse train includes first emitting a pulse that rotates the magnetization, initially polarized along the $B_0$ field, by 90° into a plane perpendicular to the $B_0$ field. A train of equally spaced pulses, whose function is to maintain the magnetization polarized in the transverse plane, follows. In between the pulses, magnetization refocuses to form the spin echo signals 16 that may be measured using the same antenna. Because of thermal motion, individual hydrogen nuclei experience slightly different magnetic environments during the pulse sequence, a condition that results in an irreversible loss of magnetization and consequent decrease in successive echo amplitudes. This rate of loss of magnetization is characterized by a "transverse relaxation time" (called T2) and is depicted by the decaying envelope 12 of FIG. 1. This may be referred to as a T2-based experiment.

The relaxation times may be used to estimate the permeability of a downhole formation. In this manner, the magnetic resonance relaxation-time of a water filled pore (of the formation) is proportional to a volume-to-surface ratio of the pore. A high surface-to-volume ratio indicates either the presence of clay minerals in the pore space or microporosity, both of which impede fluid flow. Therefore, there is a correlation between the magnetic resonance relaxation times and permeability.

Obtaining T2 times from magnetic resonance logs is an ill-posed problem. Either the precision or the resolution of the decay-time spectrum is severely limited by the signal-to-noise ratio of the measurements. Quite often, magnetic resonance logs are depth-stacked before signal processing to improve the signal-to-noise ratio of the data. Depth stacking increases the signal-to-noise ratio (SNR) by adding, or stacking, the amplitudes of corresponding spin echo signals that are obtained from different NMR measurements. For example, the amplitude of the tenth spin echo signal from a first CPMG measurement may be combined with the amplitude of the tenth spin echo signal from a second CPMG measurement. Because the tool may be moving, the CPMG measurements are performed at different depths.

The above-described depth stacking increases the signal-to-noise ratio by a factor of $\sqrt{N}$, where "N" represents the number of measurements that are combined in the depth stacking.

A problem with depth stacking is that the stacking reduces the vertical resolution of the NMR measurements. Furthermore, the NMR tool that is used to obtain the measurements for the depth stacking may move between measurements. Thus, in thinly laminated sand-shale sequences, the measurements for sand and shale layers may be stacked together, thereby making it difficult to distinguish a shaley sand from a sequence of shales and highly producible sands. There are several techniques that may used to estimate the permeability of a formation, and these techniques may include fitting the NMR signal to a model function, a technique that may increase the statistical error in the derived permeability estimator. For example, one technique to derive a permeability estimator includes representing the amplitude of each spin echo signal by a summation, as described below:

$$\text{echo}(n) \approx \sum_j A_j e^{-n\frac{TE}{T_{2,j}}}, \quad \text{(Eq. 2)}$$

where "TE" represents the echo spacing, and "$A_j$" represents the amplitude of components having a relaxation time $T_{2,j}$. A histogram 17 of the $A_j$ coefficients defines a T2 distribution, as depicted in FIG. 2. The $A_j$ coefficients may be used in two different techniques to derive a permeability indicator, as described below.

In a technique referred to as the Timur-Coates technique, a bound fluid volume (BFV) cutoff time (called $T2_{CUTOFF}$) is used. In this manner, the $A_j$ coefficients for polarization times below the $T2_{CUTOFF}$ time may be summed to derive the BFV, as described by the following equation:

$$BFV = \sum_{j=1}^{jmax} A_j, \quad \text{(Eq. 3)}$$

where "jmax" corresponds to the T2 value of a cutoff time called $T2_{CUTOFF}$. From the computed BFV, the Timur-Coates permeability (called $K_{TC}$) may be estimated using the following equation:

$$K_{TC} = \alpha \phi^m \left(\frac{\phi - BFV}{BFV}\right)^n, \quad \text{(Eq. 4)}$$

where a, m and n are adjustable parameters, and "$\phi$" represents a porosity that is obtained from analysis of the NMR data or from an independent measurement.

Another way to derive a permeability estimator using the histogram 17 is to compute a mean of the log (T2) times, often referred to as $T2_{LM}$, that is described below by the following equation:

$$\log T2_{LM} = \frac{\sum A_j \log T2_j}{\sum A_j} \quad \text{(Eq. 5)}$$

From the $T2_{LM}$ time, a permeability estimator may be derived as follows:

$$K_{SDR} = a'\phi^{m'}(T2_{LM})^{N'} \quad \text{(Eq. 6)}$$

where a', m' and n' are adjustable parameters.

A drawback of the above-described techniques is that once the NMR measurements are performed, several processing steps (such as the steps that are used to derive a distribution of relaxation times, for example) are used to derive the permeability estimator. Unfortunately, these processing steps may increase the statistical error of the derived permeability estimator.

It is also possible to derive a permeability estimate from NMR data without explicitly fitting the NMR signal. For example, U.S. Pat. No. 4,933,638, entitled "Borehole Measurement of NMR Characteristics of Earth Formations, and Interpretation Thereof," granted Jun. 12, 1990, discloses the following technique to estimate a permeability. First, several magnetization levels (called $M(tp_1)$, $M(tp_2)$, ... $M(tp_N)$) of the $M_Z$ magnetization curve are measured using several polarization times ($tp_1$, $tp_2$, ... $tp_N$). Each $M(tp_i)$ magnetization level may be described by the following equation:

$$M(tp_i) = M_0\left(\left(1 - e^{\frac{-tp_i}{T_1}}\right)\right), \quad \text{(Eq. 7)}$$

where "i" represents an integer from 1 to N. Next, the $M(tp_i)$ magnetization levels may be used to derive a piecewise linear graph that roughly approximates the $M_Z$ magnetization curve. The area (called A) under the piecewise linear graph may be calculated as described by the following equation:

$$A = \sum_{i=1}^{N-1} [M(tp_N) - M(tp_i)] \cdot (tp_{i+1} - tp_i) \quad \text{(Eq. 8)}$$

From the A area, a permeability (called K) may be calculated, using the following equation:

$$K = A^2 \phi_t^{m-2}, \quad \text{(Eq. 9)}$$

where "$\phi_t$" represents a porosity that is independently measured, and "m" represents an integer. However, this method employs T1 based measurements, which are relatively time-consuming and therefore impractical for the purposes of logging. Furthermore, Eq. 9 requires an independent measure of the porosity, $\Phi$, which may not necessarily be available.

Thus, there is a continuing need for a technique that addresses one or more of the problems that are stated above.

SUMMARY

In one embodiment of the invention, a method for use with spin echo signals that are received from a sample includes summing indications of the amplitudes of the spin echo signals. The results of the summing are used to determine an indication of a permeability of the sample, without using a distribution of relaxation times in the determination.

In another embodiment of the invention, a method for use with spin echo signals that are received from a sample includes summing products of indications of the amplitudes of the spin echo signals. The results of the summing are used to determine an indication of a permeability of the sample, without using a distribution of relaxation times in the determination.

The permeability indicator, derived by summing indications of echo amplitudes or products of echo amplitudes, may be used to provide a qualitative indication of formation quality to aid in establishing potential reserves.

Advantages and other features of the invention will become apparent from the following description, drawing and claims.

BRIEF DESCRIPTION OF THE DRAWING

FIG. 7 is a graph illustrating a permeability estimation according to an embodiment of the invention for different numbers of spin echoes.

FIG. 9 is a schematic diagram of a wireline system according to an embodiment of the invention.

FIG. 10 is a schematic diagram of a logging while drilling system according to an embodiment of the invention.

DETAILED DESCRIPTION

Figure 1:
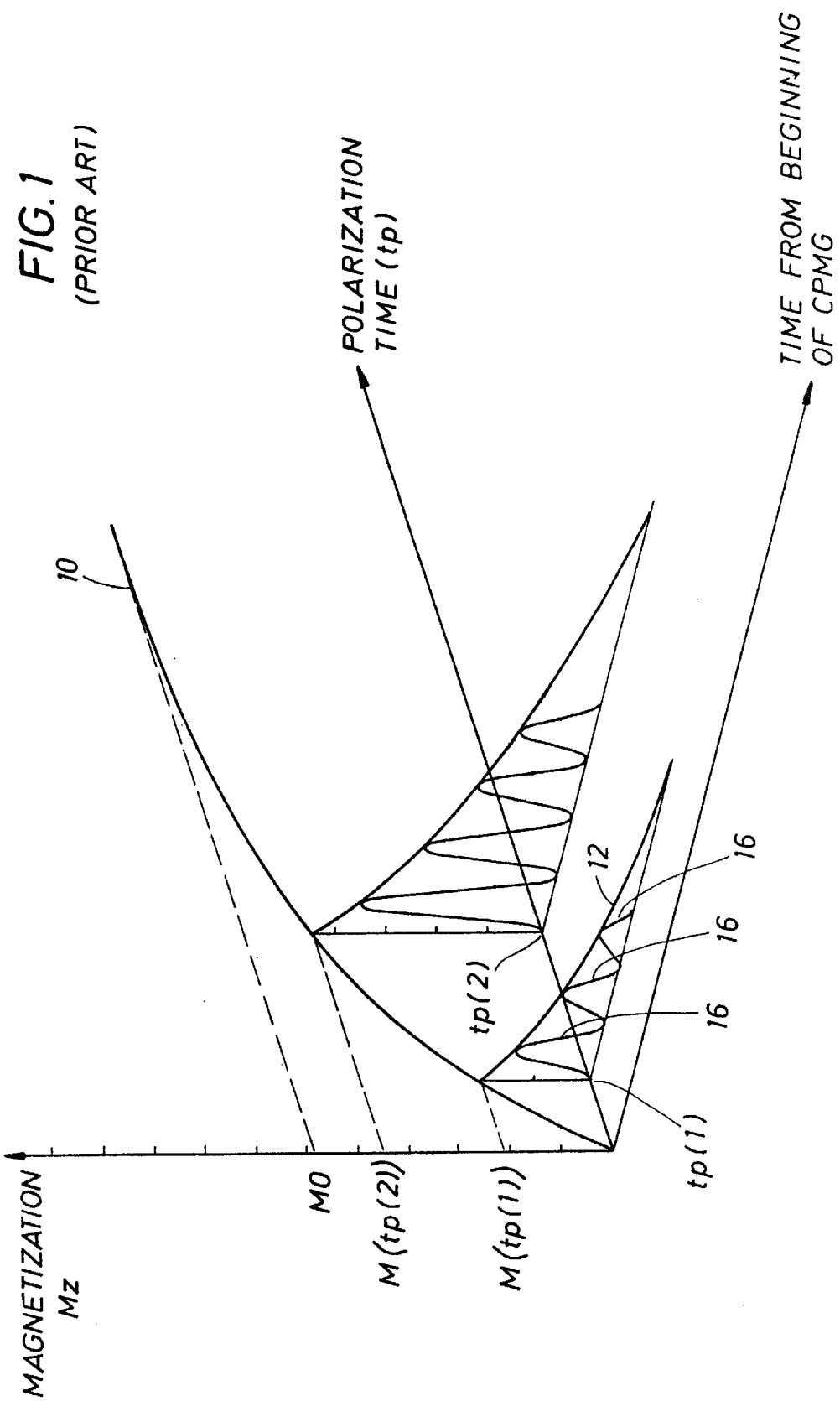
FIG. 1 is a diagram illustrating T1-based and T2-based measurements of the prior art.
Figure 3:
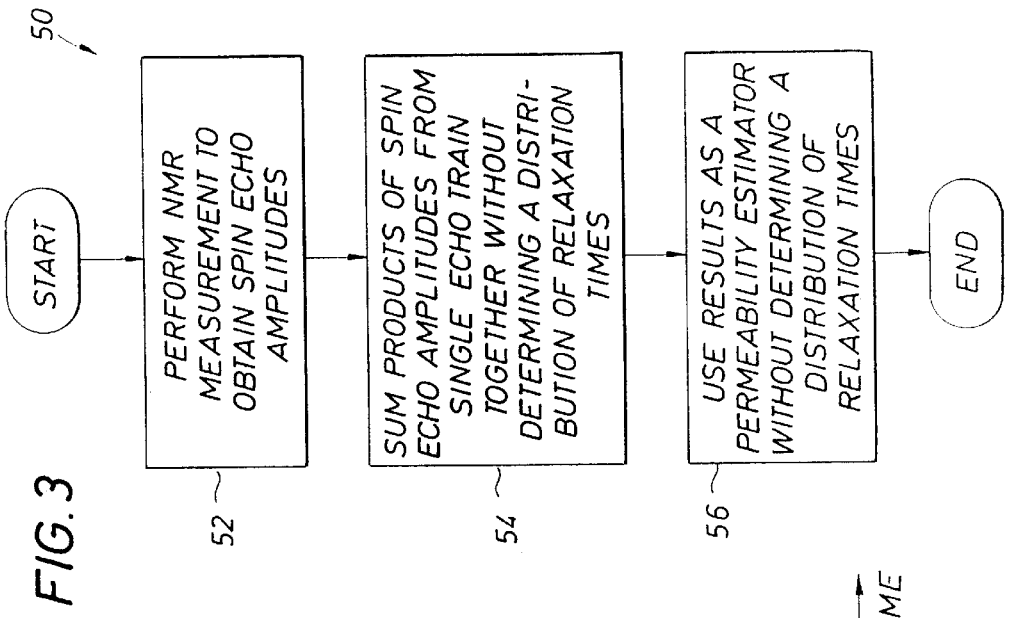
FIG. 3 is a flow diagram illustrating a technique to derive a permeability estimator according to an embodiment of the invention.
Figure 2:
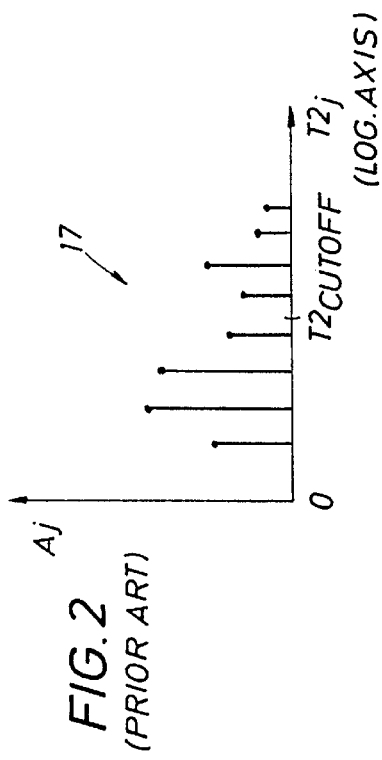
FIG. 2 is a histogram of coefficients that indicate a T2 distribution according to the prior art.
Figure 4:
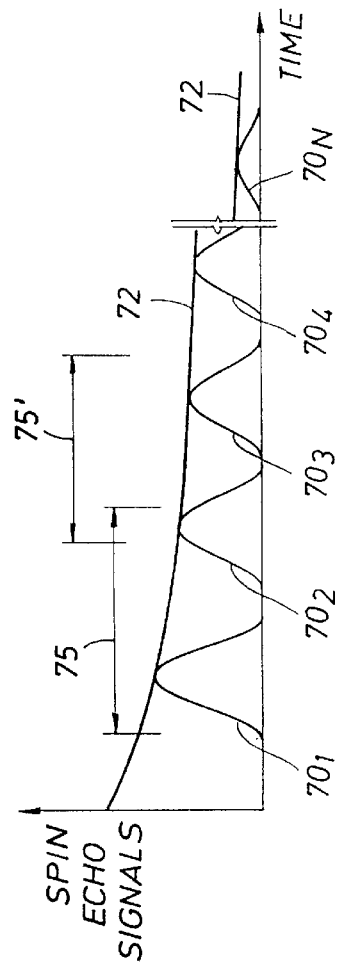
FIG. 4 is a graph of spin echoes from an NMR measurement.

Referring to FIG. 3, an embodiment 50 of a technique to derive a permeability estimator in accordance with the invention includes performing (block 52) a nuclear magnetic resonance (NMR) measurement to obtain spin echo amplitudes, such as amplitudes of spin echo signals $70_1$, $70_2$, $70_3$, ..., $70_N$ (see FIG. 4) that decay pursuant to a profile 72. It has been discovered that by summing (block 54) the spin echo amplitudes or summing the products of the spin echo amplitudes of a single echo train together, the resultant summed value may be directly used (block 56) as a permeability estimator, as described below. Thus, as a result of this arrangement, deriving the permeability estimator involves a minimum number of processing steps and does not involve determining a distribution of relaxation tires. Therefore, nonlinear/linear inversion of the measured data may not be required. Furthermore, porosity does not need to be independently measured, thereby eliminating the need for a porosity measuring tool. Additionally, the above-described technique yields a high resolution estimate of permeability because depth stacking is not used.

More particularly, a summation (called p) of spin echo amplitudes that is produced by a CPMG sequence may be described by the following equation:

$$p = \sum_{n=1}^{N} \text{echo}(n) = \sum_{n=1}^{N} \left[ \text{noise}(n) + \int_0^\infty A(T_2)\exp(-nTE/T_2)dT_2 \right], \quad \text{(Eq. 10)}$$

where "$A(T_2)dT_2$" represents that product of the hydrogen index and the volume fraction of the fluid whose relaxation time is between $T_2-dT_2/2$ and $T_2+dT_2/2$; the index "n", which labels the echoes, is an integer from 1 to N (the number of echoes in the CPMG sequence); and "TE" represents the echo spacing in seconds. In Eq. 10, "echo(n)" represents the amplitude of the nth spin echo, and "noise(n)" represents the zero-mean random additive noise in the measurement. The random part of the p summation may be labeled "ξ", a component that is described by the following equation:

$$\xi = \sum_{n=1}^{N} \text{noise}(n) \quad \text{(Eq. 11)}$$

Thus, using this notation, the p summation may be alternatively expressed as:

$$p = \xi + \int_0^\infty A(T_2)[1 - \exp(-NTE/T_2)]/[1 - \exp(-TE/T_2)] \exp(-TE/T_2)dT_2 \quad \text{(Eq. 12)}$$

The expectation value of p is a weighted integral of the relaxation-time distribution. The weighting function is given by the following expression:

$$w(T_2/TE,N) \equiv [1-\exp(-N\,TE/T_2)]/[1-\exp(-TE/T_2)]\exp(-TE/T_2) \approx T_2/TE. \quad \text{(Eq. 13)}$$

The approximation on the second line of Eq. 13 is valid when $TE \ll T_2 < N\,TE$. In that case, the p summation may be alternatively expressed as:

$$p \approx \xi + \int_0^\infty A(T_2)(T_2/TE)dT_2 = \xi + HI\Phi\langle T_2 \rangle/TE, \quad \text{(Eq. 14)}$$

where "Φ" represents the porosity, and "HI" represents the hydrogen index. For simplicity, the discussion herein refers to a single fluid phase. "$\langle T_2 \rangle$" represents the mean-relaxation time, a time that is distinct from the log-mean-relaxation time that is commonly used in magnetic resonance logging. Because the permeability of a formation is an increasing function of both the porosity, Φ, and the mean relaxation time, $\langle T_2 \rangle$, the p summation of spin echo amplitudes may be directly used as a permeability indicator.

Figure 5:
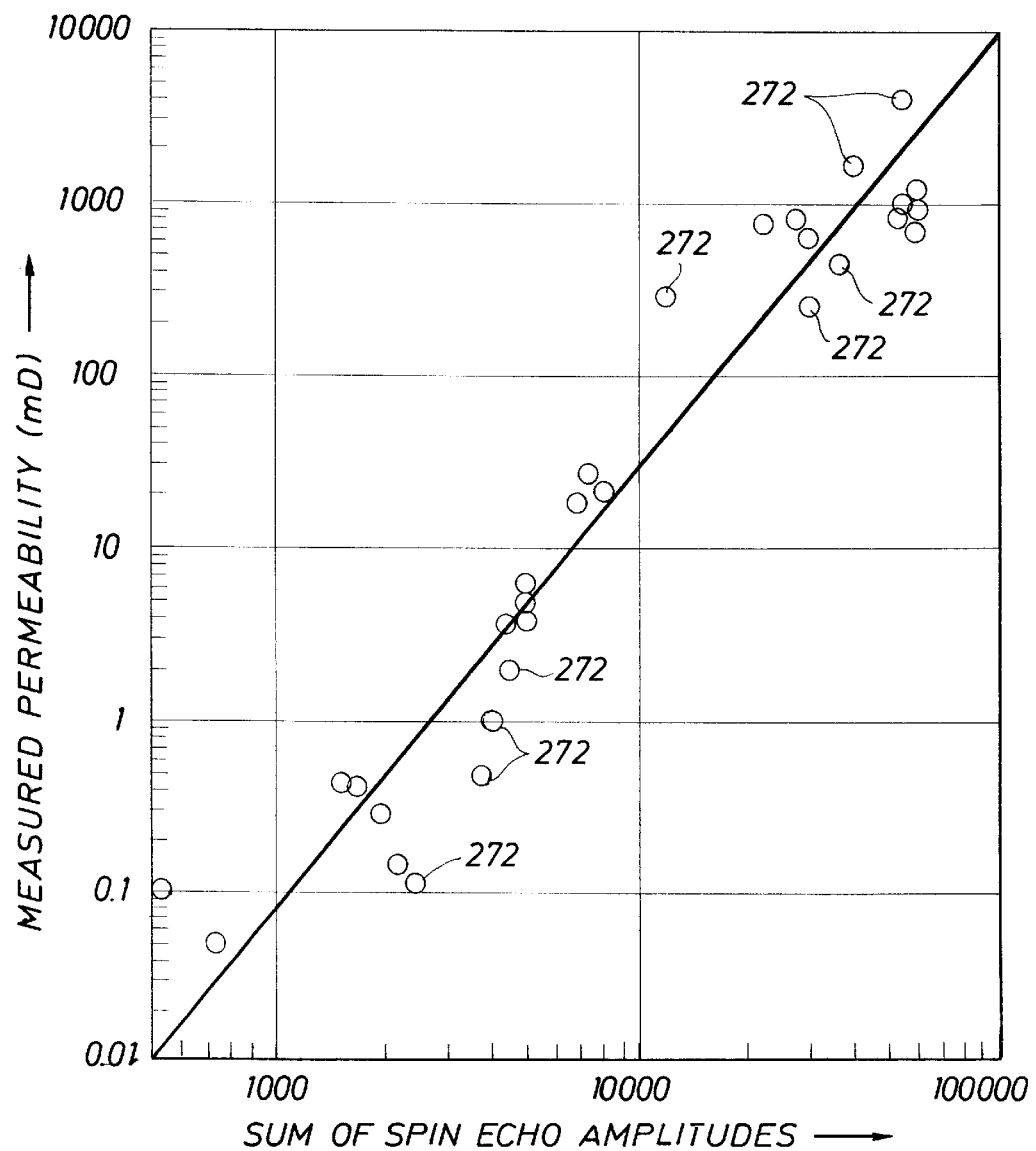
FIG. 5 is a plot illustrating a relationship between permeability and the sum of spin echo amplitudes.

As described above, the permeability indicator is an increasing function of porosity. It is also an increasing function of the volume-to-surface ratio in a water filled clastic formation, which is correlated to its permeability. Increasing clay content decreases p, and the better the quality of the reservoir, the higher is the permeability indicator. The two commonly used methods of estimating the permeability from magnetic resonance logs are based on correlations and may be accurate to one order of magnitude. By correlating p with standard permeability measurements 272 on controlled samples, as illustrated in FIG. 5, a quantitative estimate of permeability may be derived. The quantitative estimate is derived from p using the empirical relationship:

$$K = a''p^b \quad \text{(Eq. 15)}$$

where a" and b are determined by fitting the measured permeability data. In this way, the sum of echo amplitudes permeability estimator may be calibrated to provide a quantitative permeability.

Measurements that have been performed with NMR logging instruments indicate that the noise in the echoes has a zero mean and is uncorrelated, as described by the following equations:

$$E[\text{noise}(n)]=0 \text{ and} \tag{Eq. 16}$$

$$E[\text{noise}(n) \text{ noise}(m)]=\sigma^2 \delta_{nm}, \tag{Eq. 17}$$

where "E[x]" denotes the expectation (ensemble average) of the random variable x. The variance of p is:

$$\text{Var}[p]=\text{Var}[\xi]=N\sigma^2, \tag{Eq. 18}$$

and the signal-to-noise ratio (SNR) of the sum of echoes is:

$$SNR[p]=HI\Phi<T_2>/(TE\ N^{1/2}\sigma) \tag{Eq. 19}$$

Figure 6:
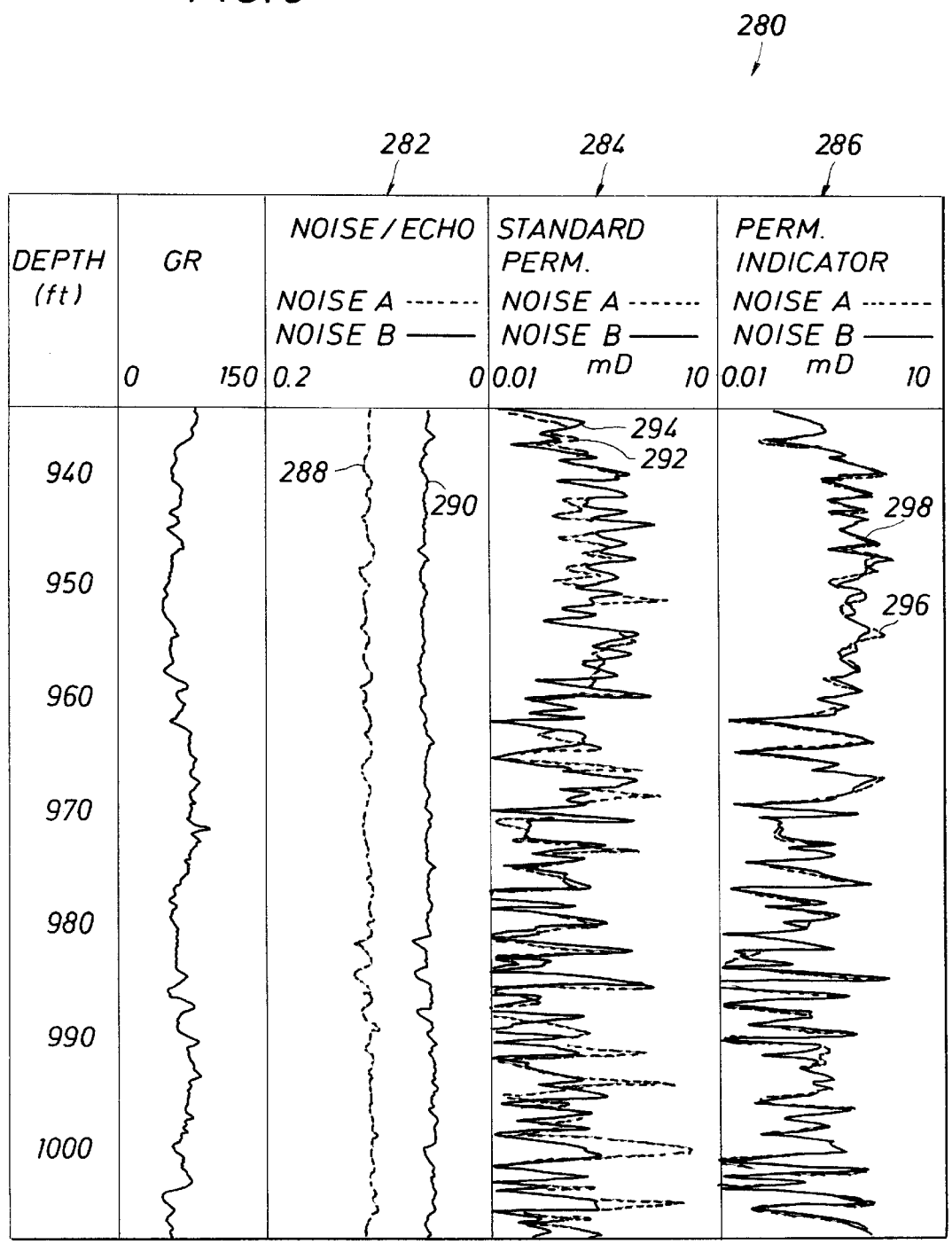
FIG. 6 is a schematic diagram of an NMR measurement log illustrating the noise insensitivity of the sum of spin echo amplitudes.

For most cases of practical interest, the precision of the sum of echoes, p, is substantially higher than that typically found for standard NMR permeability estimates based on measurements of both the porosity and relaxation behavior. This improved precision is illustrated by an NMR measurement log 280 of FIG. 6. The log 280 includes a noise per echo track 282 that shows two different plots 288 and 290. The lower noise plot (290) is the noise per echo derived from raw log data. The higher noise plot (288) was derived from the same data, to which synthetic zero-mean Gaussian noise was added. The two data sets (i.e. the original raw data and the raw data with added noise) were then processed to yield conventional permeability estimates and permeability estimates derived from the sum of spin echo amplitudes. A track 284 of the log 280 depicts plots 292 (corresponding to the noise plot 288) and 294 (corresponding to the noise plot 290) that are derived from using conventional permeability computations. Another track 286 of the log 280 depicts plots 296 (corresponding to the noise plot 288) and 298 (corresponding to the noise plot 290) that are derived from permeability computations that use the sum of spin echo amplitudes. As shown, the sum of spin echo amplitudes technique is less sensitive to noise. Thus, these results show permeability estimates derived from datasets with identical signal decays but with different realizations of zero mean Gaussian random noise. Whereas the standard permeability estimates ($K_{SDR}$) display significant variations between the two datasets due to the effects of the different noise components, the permeability that is determined using the sum of echo amplitude technique is relatively unaffected by the noise.

Because of the high SNR of the sum of echoes, there is no necessity to perform vertical averaging of the acquired logging data and therefore it is possible to obtain permeability estimates at the highest resolution of the logging tool. For example, a sensor that has a 4 inch (in.) high aperture may travel approximately 1.2 in. during the acquisition of 1000 echoes at a vertical logging speed of approximately 1800 ft/hr. For this example, the 1000 echoes are spaced apart by 0.2 milliseconds (ms) spacing and are acquired in 0.2 s. The vertical resolution, which is the sum of the sensor aperture and the distance traveled, is 5.2". On the other hand, if the mean relaxation time is short, such as 2 ms, SNR[p] is less than the SNR of a single echo. In general, the SNR of the permeability indicator may rapidly decrease as the permeability indicator itself decreases.

More particularly, FIG. 7 depicts curves 200 (curves 200$_1$, 200$_2$, ... 200$_N$, as examples), each of which represents a sum of echoes as a function of T2/TE for a unity value of HI·Φ. The number of echoes taken increases from the bottom curve 200$_1$ to the top curve 200$_N$. A dashed line 202 depicts T2/TE, the approximate value of the P summation. As shown, for large T2 values, the sum of echoes saturates at (HI Φ N) as shown in FIG. 7. As an example, the approximation in Eq. 14 may hold for 1<T2/TE<100 for N=100.

The petrophysical implication from FIG. 7 is that two rocks of identical porosity and fluid content but distinct permeabilities become indistinguishable for large T2 values. These large T2 values, in turn, correspond to large values of permeability. Thus, there may be a limitation of the indicator obtained by summing the echoes, and the larger the number of echoes in the CPMG sequence, the wider is the range of validity of the approximation that is used in Eq. 13.

In favor of the approximation Eq. 13, the sum of the spin echo amplitudes is a continuous, monotone increasing function of T2 and is a linear function of (HI·Φ. The relationship never goes in the wrong direction. Also in defense of approximation in Eq. 13, the relaxation time T2 of a porous rock saturates as the pore size increases. The relaxation time of the fluid filled porous rock cannot exceed the bulk relaxation of the fluid influenced by diffusion:

$$(1/T2)_{APPARENT}=(1/T2)_{BULK}+D(TE\ \gamma G)^2/12+\rho S/V, \tag{Eq. 20}$$

where "D" represents the effective molecular diffusion coefficient, "G" represents the magnetic field gradient, "ρ" represents the surface relaxivity, "γ" represents the gyromagnetic ratio, and "S/V" denotes the surface to volume ratio of a pore. Restrictions on the diffusion of fluid molecules are ignored in Eq. 20. As the permeability increases, the S/V term gets smaller, and eventually, the first two terms on the right hand side of Eq. 20 dominate. Since T2 is bounded from above as permeability increases, a producibility index that saturates for corresponding high in values of T2 is not a significant limitation.

Figure 8:
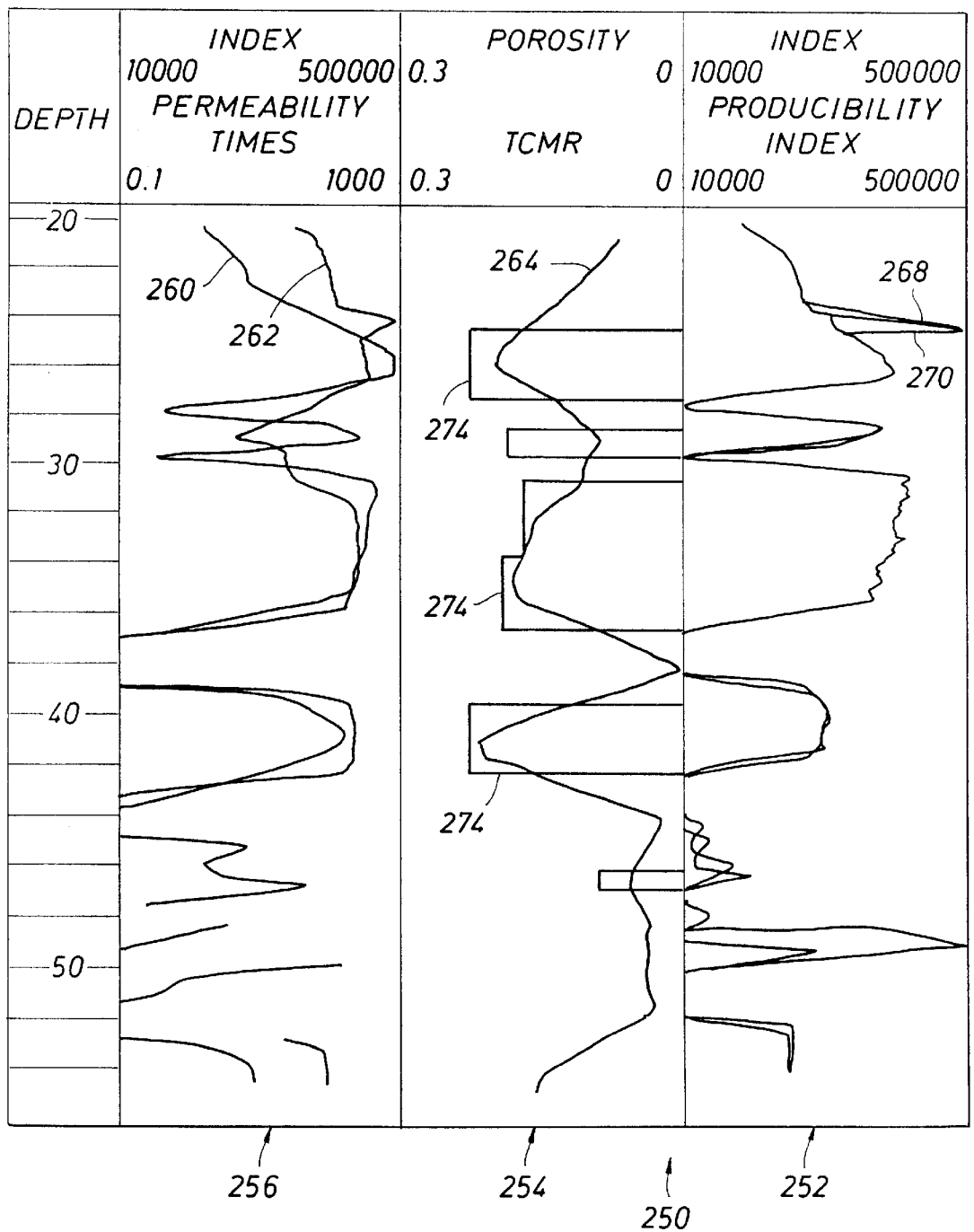
FIG. 8 is an NMR measurement log depicting different techniques to estimate permeability.

FIG. 8 depicts a log 250 (of three tracts 252, 254 and 256) that was obtained by using an NMR measurement tool in a test pit that has an artificial formation made of blocks of quarried rocks. The track 252 on the right depicts two different graphs 268 and 270 (of the above-described producibility index) that were obtained in two successive logging passes. The track 254 in the center depicts a continuous porosity graph 264 over the entire depth, and the discontinuous graph portions 274 depict the porosity of core plugs taken from the rocks.

The track 256 on the left includes a graph 262 that is derived from the above-described permeability estimator of the present invention and a graph 260 that is derived from the Timur-Coates computation of permeability. As shown, these two permeabilities are closely correlated.

However, the vertical resolution of the graph 262 is significantly higher than that of the Timur-Coates permeability graph 260.

The above-described technique to derive the permeability estimator may be generalized, as described by the following equations:

$$p = \sum_n G_j^a(n+k) G_m^b(n), \tag{Eq. 21}$$

where $$G_m(n) = \sum_{i=1}^{N} G_{m-1}(i) G_{m-1}(i+n); \tag{Eq. 22}$$

$$G_1(n)=M(n); \tag{Eq. 23}$$

$$G_0(n)=1; \tag{Eq. 24}$$

a and b are exponents; i, j, k, m, n are integers; and M(n) is a measure of the amplitude of the nth echo. Therefore, the previously described technique implies a=b=1, m=1, j=0 and k=0.

Another instance of Eq. 21 is where a=b=1, m=j=1 and k=0. This represents the sum of the squares of the echo amplitudes. In this case, and in other instances where the even powers of echoes are summed, noise components are rectified. To overcome this problem, the product of successive (in time) spin echo amplitudes are taken and added to the total summation. This would correspond to Eq. 21 with a=b=1, m=j=1 and k=1.

For example, referring back to FIG. 4, instead of summing echo amplitudes that are each squared, a sliding window of two spin echo amplitudes may be used. In this manner, the product of the spin echo amplitudes $70_1$ and $70_2$ within the window 75 is taken, and the window 75 slides as indicated by reference numeral 75' to encompass amplitudes of the spin echoes $70_2$ and $70_3$. The product of the amplitudes of the spin echoes $70_2$ and $70_3$ is taken and added to the product of the amplitudes of the spin echoes $70_1$ and $70_2$. The noise is not rectified using this technique. This technique may also be used to sum up spin echo amplitudes that are raised to another even power.

In the context of this application, the term "spin echo amplitude" refers to an amplitude that is formed in the following manner:

$$\text{echo}(n) = I(n) \cdot \cos\theta + Q(n) \cdot \sin\theta, \quad \text{(Eq. 25)}$$

where I(n) is an in-phase component and Q(n) is a quadrature component of the echo(n) amplitude. The phase angle, θ, is usually estimated using the following expression:

$$\theta = \tan^{-1}\left[\frac{\sum_n Q(n)}{\sum_n I(n)}\right] \quad \text{(Eq. 26)}$$

Because Q(n) and I(n) contain noise as well as signal components, the precision with which θ may be obtained is limited, inevitably leading to some statistical error in any quantities computed from the phased data. This error may be eliminated by summing even powers of echo amplitudes. For example, one procedure to derive a permeability-related quantity with zero phase error and zero mean noise (i.e., without noise rectification) is to compute the following summation:

$$p' = \sum_n I(n)I(n+1) + Q(n)Q(n+1) \quad \text{(Eq. 27)}$$

Other similar summations of even powers of echo amplitudes can also be computed, which provide zero mean noise and zero phase error.

Figure 11:
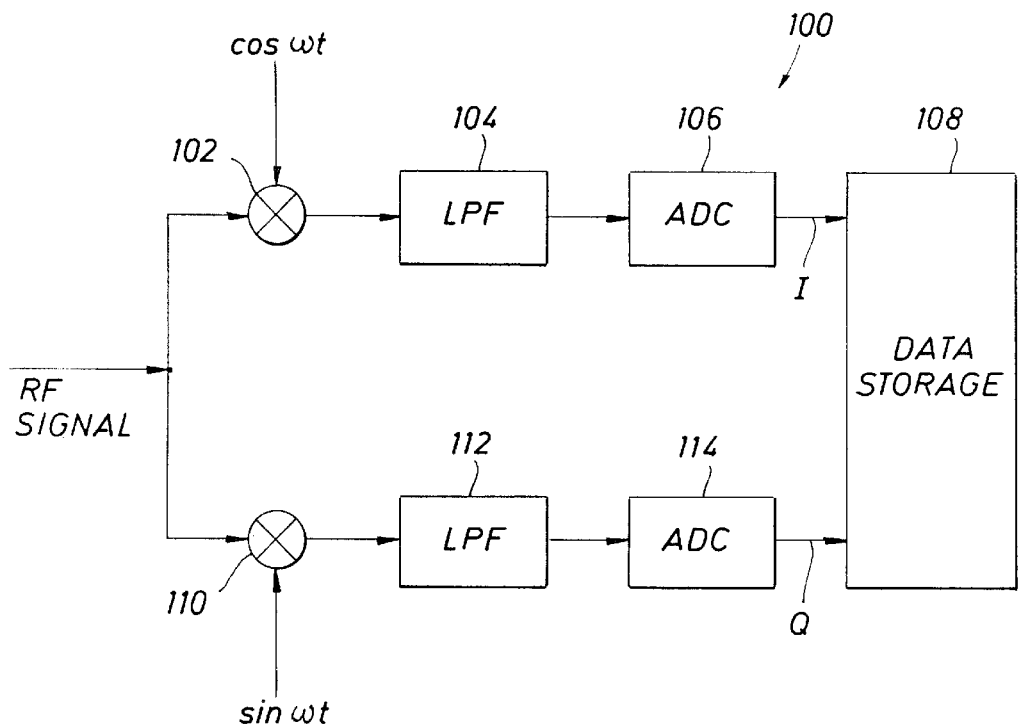
FIG. 11 is a block diagram of a system to obtain spin echo amplitudes from a received RF signal.

A system 100 that is depicted in FIG. 11 may be used, in some embodiments, to derive the I and Q components. For purposes of generating the I component, the system 100 may include a multiplier 102 that receives a radio frequency (RF) signal from the receive antenna that is used in the performance of the NMR measurement. The multiplier 102 multiplies the RF signal by cosωt, where "ω" represents a carrier frequency of the RF signal. The resultant signal is received by a low pass filter (LPF) 104. The output signal of the LPF 104 is digitized by an analog-to-digital converter (ADC) 106 to produce the I component. For purposes of generating the Q component, the system 100 may include a multiplier 110 that receives the RF signal from the receive antenna and multiplies the RF signal by sinωt. The resultant signal is received by a LPF 112. The output signal of the LPF 112 is digitized by an ADC 114 to produce the Q component. As an example, the I and Q components may be stored in data storage 108 until processed.

As examples, in different embodiments, the NMR measurement tool may be a wireline tool 62 (as depicted in FIG. 9) or a logging while drilling (LWD) tool 68 (as depicted in FIG. 10) that is part of a drill string 65. As an example, the wireline tool 62 may transmit signals indicative of NMR measurement data to a computer 300 that is located at the surface of the well. A program 302 that is stored on the computer 300 may cause the computer 300 to perform the above-described stacking technique to derive the permeability estimator.

Figure 12:
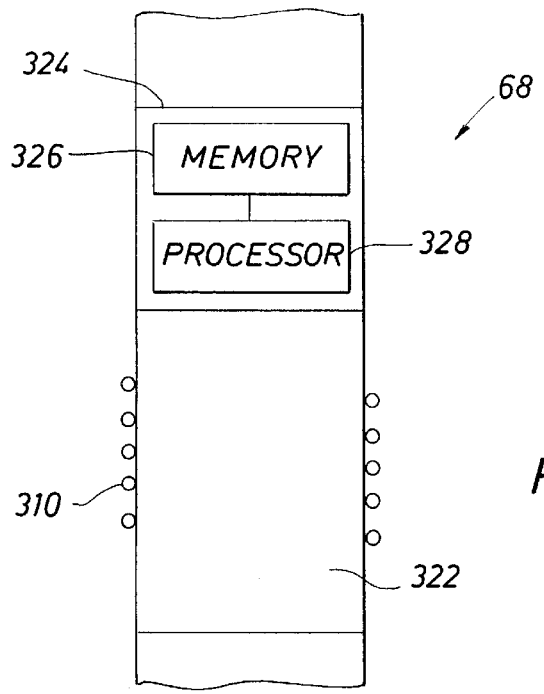
FIG. 12 is a schematic diagram of a downhole NMR tool of FIG. 10.

As another example, in some embodiments, referring to FIG. 12, the LWD tool 68 may include a memory 326 (part of circuitry 324 of the LWD tool 68) that stores a program (such as the program 302). This program may cause a processor 328 of the LWD tool 68 to derive the permeability estimator, as described above. Among the other features of the LWD tool 68, the tool 68 may include a permanent magnet 322 to establish a static magnetic field and at least one transmit/receive coil, or antenna 310. In this manner, the processor 328 may be coupled to the antenna 310 to receive spin echo signals. In some embodiments, the program may cause the processor 328 to sum indications of amplitudes of the spin echo signals and use the sum to determine an indication of a permeability of the sample without using a distribution of relaxation times in the determination. In some embodiments, the program may cause the processor 328 to sum products of indications of amplitudes of the spin echo signals and use the sum to determine an indication of a permeability of the sample without using a distribution of relaxation times in the determination. The circuitry 324 also may implement the system 100 that is depicted in FIG. 11. The LWD tool 68 is merely an example and is not intended to limit the scope of the claims.

While the invention has been disclosed with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. A method for use with NMR spin echo signals received from a sample in a well logging application, comprising;
   summing products of indications of amplitudes of the spin echo signals, wherein the summing is performed without using a distribution of relaxation times, and
   using the results of the summing to determine an indication of a permeability of the sample also without using a distribution of relaxation times in the determination.

2. The method of claim 1, wherein the summing does not use a nonlinear inversion of the spin echo amplitudes to the relaxation times.

3. The method of claim 1, wherein the summing does not use a linear inversion of the spin echo amplitudes to the relaxation times.

4. The method of claim 1, wherein each indication comprises an indication of one of a the amplitudes raised to a power.

5. The method of claim 4, wherein the power comprises an odd power.

6. The method of claim 4, wherein the power comprises an even power.

7. The method of claim 1, further comprising:
   calibrating the determined permeability with measured permeability data.

8. A well logging NMR measurement apparatus comprising:
- at least one antenna to receive NMR spin echo signals from a sample;
- a processor coupled to said at least one antenna; and
- a memory storing a program to cause the processor to:
   - sum products of indications of amplitudes of the spin echo signals, wherein the summing is performed without using a distribution of relaxation times, and use the sum to determine an indication of a permeability of the sample also without rising a distribution of relaxation times in the determination.

9. The NMR measurement apparatus of claim 8, wherein the apparatus comprises a logging while drilling tool.

10. The NMR measurement apparatus of claim 8, wherein the apparatus comprises a wireline tool.

11. The NMR measurement apparatus of claim 8, wherein the processor does not use a nonlinear inversion of the spin echo amplitudes to the relaxation times to determine the indication of the permeability.

12. The NMR measurement apparatus of claim 8, wherein the processor does not use a linear inversion of the spin echo amplitudes to the relaxation times to determine the indication of the permeability.

13. The NMR measurement apparatus of claim 8, wherein each indication comprises an indication of one of the amplitudes raised to a power.

14. The NMR measurement apparatus of claim 13, wherein the power comprises an odd power.

15. The NMR measurement apparatus of claim 13, wherein the power comprises an even power.

* * * * *